United States Patent [19]

Uffenheimer

[11] Patent Number: 4,629,703

[45] Date of Patent: Dec. 16, 1986

[54] AUTOMATED ANALYTICAL SYSTEM

[75] Inventor: Kenneth F. Uffenheimer, Mahopac, N.Y.

[73] Assignee: Technicon Instruments Corporation, Tarrytown, N.Y.

[21] Appl. No.: 458,071

[22] Filed: Jan. 14, 1983

Related U.S. Application Data

[62] Division of Ser. No. 296,760, Aug. 27, 1981, abandoned.

[51] Int. Cl.[4] ............... G01N 31/22; G01N 35/04
[52] U.S. Cl. ................... 436/45; 422/63; 422/64; 436/47; 436/164
[58] Field of Search .................... 422/64–67, 422/72, 73; 436/45, 47, 164, 165; 494/16

[56] References Cited

U.S. PATENT DOCUMENTS

| | | | |
|---|---|---|---|
| 3,615,222 | 10/1971 | Mead | 422/71 |
| 3,718,439 | 2/1973 | Rosse et al. | 422/102 |
| 3,829,223 | 8/1974 | Hamel | 422/72 |
| 4,058,367 | 11/1977 | Gilford | 422/67 |
| 4,135,883 | 1/1979 | McNeil et al. | 494/16 |
| 4,225,558 | 9/1980 | Peterson et al. | 422/72 |
| 4,313,735 | 2/1982 | Yamashita | 422/67 |
| 4,325,910 | 4/1982 | Jordan | 422/64 |

FOREIGN PATENT DOCUMENTS 52-40189  3/1977  Japan .................... 422/64

Primary Examiner—Michael S. Marcus
Attorney, Agent, or Firm—James R. Cartiglia

[57] ABSTRACT

A discrete-type analytical system comprising a cuvette tray which is adapted for bidirectional rotation, so as to ensure accurate repositioning of individual reaction cuvettes at one or more treatment stations.

17 Claims, 3 Drawing Figures

AUTOMATED ANALYTICAL SYSTEM

This application is a division of application Ser. No. 296,760, filed Aug. 27, 1981, abandoned.

BACKGROUND OF THE INVENTION

1. Field of the Invention

The invention relates to automated discrete type biochemical analytical systems wherein a reaction cuvette tray is adapted for bidirectional rotational movement, such as to effect and precisely measure zero-order and first order rate reactions and, also, end-point reactions. The bidirectional rotational movement insures a proper repositioning of each of the individual cuvettes supported on such tray at the treatment stations.

2. Description of the Prior Art

In the field of automated biochemical analytical systems, wherein samples are reacted and analyzed in respect of one or more analytes, it is often desirable that the analyses be performed on a selective basis in respect of each sample. Because of the high demand of clinical laboratories, it is required that such systems should provide, in addition to accurate analytical results, a high thru-put and versatility and, also, low reagent consumption to reduce the cost per input test.

Present-day analytical systems may be divided into two categories. One such category includes the continuous-flow analytical systems, such as described in the L. Skeggs et al U.S. Pat. No. 3,241,341 and the W. Smythe et al U.S. Pat. No. 3,479,141, both assigned to a common assignee. In such systems, continuous streams of successive sample segments and reagent are introduced, at properly related flow rates, into the system and passed along an analytical channel, wherein the successive samples are reacted and analyzed in respect of a same analyte. As described, the stream of sample segments can be divided, or split, into a number of aliquot streams, which are directed each along an individual analytical channel to be reacted and analyzed in respect of a particular analyte. The analytical results derived from the analytical channels are thereafter correlated in respect to the patient or source. While such systems as described in the Skeggs et al patent are not selective, in that a fixed battery of analyses are performed, such systems do exhibit an extremely high thru-put and are capable of satisfying the test requirements of large clinical laboratories. However, the Smythe et al patent describes a continuous-flow system of high thru-put, wherein selectivity is obtained by injecting or introducing, on a selective basis and on in-line fashion, precise volumes of reagents to react with successive sample segments flowing in a continuous stream.

The second category includes discrete-type analyzers, wherein properly related volumes of sample and reagent are introduced into a reaction cuvette, the resulting reaction product being measured to determine the concentration of the analyte. Such systems may be adapted to perform a single type of analysis, termed a batch-type system, or to perform different types of analyses in respect of the individual samples. In such systems, a plurality of reaction cuvettes can be formed into an integral reaction tray, for example as described in U.S. application Ser. No. 284,845, filed July 20, 1981 and assigned to a common assignee. Such tray is rotated to advance each cuvette, in turn, between a reagent addition station, a sample addition station, and an analytical or read-out station.

To obtain maximum versatility, discrete-type systems are often adapted to perform different types of analyses, so as to quantitate various analytes of interest present in biological samples. Such types of reactions can be divided into three types. The first type of reaction can be described as a zero-order rate reaction, as performed in respect as aspartate aminotransferase, alkaline phosphatase, etc., wherein the concentration of the reaction product to be measured varies linearly with time. The second type of reaction can be defined as a first-order rate reaction, as performed in respect of urea nitrogen, creatinine, etc., wherein the concentration of the reaction product varies non-linearly with time. The third type of reaction can be defined as an end-point reaction, as performed in respect of glucose, total protein, etc., wherein the reaction goes to completion before measurement. As is appreciated, analyte quantitation in respect of each of such reactions requires that multiple measurements be made, e.g., colorimetrically, of the reaction product. To achieve highly accurate results, therefore, it is essential that such multiple measurements be made in respect of each individual cuvette, whether supported individually or integrally formed in the reaction tray, uncer identical conditions. Unless this is achieved, accuracy of the analytical result is reduced.

Generally, reaction cuvettes used in discrete-type analytical systems are formed of plastic or glass. As each cuvette is located, in turn, at the read-out station, a beam of light of predetermined wavelength, depending upon the analyte to be quantitated, is passed therethrough and along a sight path of controlled length extending through the reaction mixture. Any variation in the thickness or quality of any imperfections or residues on the cuvette walls defining the sight path would materially affect the light transmissive properties of the cuvette. Hence, any misalignment of the individual cuvette during the multiple readings would change the proper relationship of the successive analytical results, or read-outs, with respect to the reference base-line, which is itself determined by a read-out process.

Hence, unless each individual cuvette is precisely repositioned or aligned at the read-out station, the quantitation of the analyte would not be accurate. The present invention positively insures an accurate repositioning or alignment of the cuvettes in a reaction tray at the read-out station, or at any other station or location, whereby successive analyte measurements are made under identical conditions and accuracy of the analyte measurement is insured.

SUMMARY OF THE INVENTION

Accordingly, it is an object of the present invention to provide an automated discrete-type analytical system capable of effecting highly accurate analytical measurements.

Another object of the present invention is to provide an automated discrete-type analytical system for obtaining precise repetitive positionings of reaction cuvettes supported on a tray-like structure at a read-out or other treatment station.

A further object of the present invention is to provide for the accurate positioning of an indexible turntable or tray arrangement which is rotated through a sequence of angular positions and which requires, for proper operation, the sequential repositioning of each turntable or tray at a particular position.

A further object of the present invention is to provide an automated discrete-type analytical system having an improved operation.

A still further object of the invention is to provide for the accurate repositioning of the indexible cuvette tray or turntable at a particular location, regardless of the number of times which such cuvette tray is displaced from such location.

In present-day automated discrete-type analyzers, a reaction tray comprising a plurality of cuvettes is rotated unidirectionally to successively advance each cuvette, in turn, between different treatment stations, i.e., a reagent-addition station, a sample-addition station, and a read-out station. To reposition a cuvette at a particular treatment station, it is required that the reaction tray effect a full revolution. Usually, the reaction tray is indexed by a stepping motor coupled via toothed drive belt and a toothed pulley arrangement. However, it has been concluded that positional errors are introduced in the repositioning process due to tooth-to-tooth dimensional errors in the drive belt or gear arrangement, which may be inherent imperfections or result from wear. These dimensional errors and unpredictable and result in a misalignment of the individual cuvettes in the respositioning process. In the case of the read-out station, the result is that the same opposing wall portions of the individual cuvette do not define the sight path during successive measurements, or read-outs, whereby the reliability of the analytical results, particularly in the case of zero-order and first-order rate reaction, is not optimal.

The present invention appreciates that such respositioning errors can be very substantially avoided, if the same sections of toothed drive belt and drive pulleys are used in respect of the successive repositionings of the individual cuvettes. This is achieved by adapting the reaction tray to be rotated bidirectionally, whereby a same section of the drive belt is used to displace and reposition the individual cuvettes at the read-out station. Although a unidirectional rotation of the reaction tray would be less costly to implement and would not extend the operational cycle, the bidirectional rotation of the cuvette insures that multiple readings of individual cuvettes at the read-out station are made under identical conditions and that highly reliable analytical results are obtained, as hereinabove described.

DETAILED DESCRIPTION OF THE INVENTION

Figure 1:
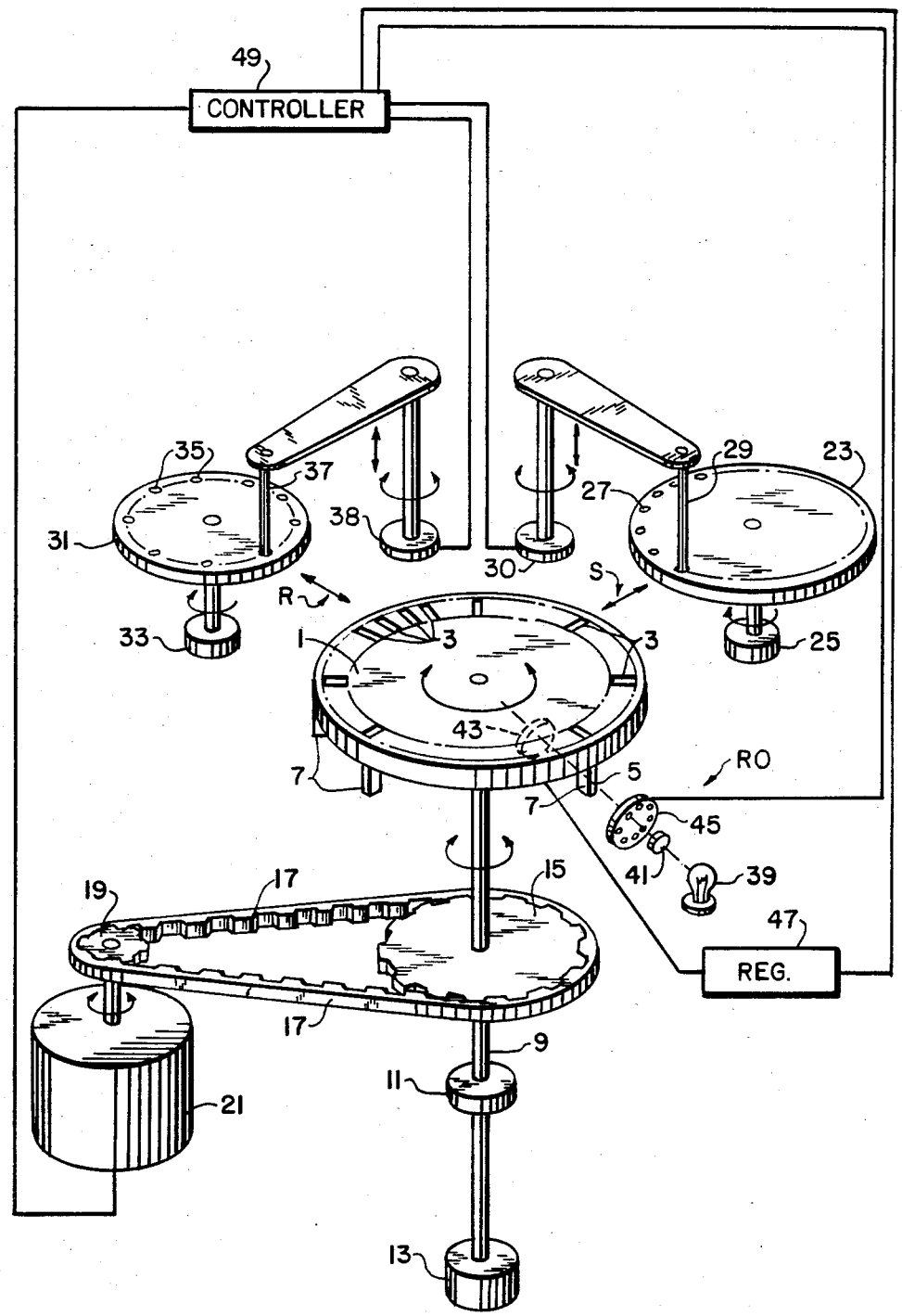
FIG. 1 is a diagrammatic view of a discrete-type biochemical analyzer according to the present invention.

Referring now to FIG. 1, a discrete-type biochemical analytical system is illustrated, which includes a circular reaction tray 1 comprising a plurality of reaction cuvettes 3. Preferably, reaction tray 1 may be of the type described in U.S. application Ser. No. 284,845, filed July 20, 1981, wherein cuvettes 1 are integrally formed and circularly arranged about the axis of rotation. Each cuvette 3 has an open upper end and at least two radially aligned opposing transparent walls 5 and 7.

Tray 1 is removably mounted and keyed on a vertical shaft 9 supported by bearings 11 and 13. Shaft 9 carries a toothed pulley 15, which is engaged by a toothed drive belt 17 driven by toothed drive pully 19 carried on the shaft of a reversible stepping motor 21. Motor 21 is operative to rotate tray 1 in either a clockwise or counterclockwise direction, as indicated by the arrow, through a sequence an angular positions.

The samples to be successively analyzed are carried on a sample tray 23 disposed adjacent to reaction tray 1 and mounted on the shaft of an AC synchronous motor 25. Sample tray 23 comprises a plurality of sample receptacles 27 arranged in circular fashion about the rotational axis of such tray. Motor 25 is operative to unidirectionally index sample tray 23, to successively advance receptacles 27, in turn, to a take-off position below an aspirating/dispensing probe 29. Probe 29 is adapted, under the control of drive mechanism 30, for vertical reciprocal and for bidirectional rotational movement, as indicated by the arrows, so as to be selectively positioned over and immersed into a receptacle 27 and into a cuvette 3 advanced to sample-dispense station S. Probe 29 operates to aspirate a precise aliquot of the sample contained in such receptacle 27 and to dispense or load the same into such cuvette 3.

Also, a reagent tray 31 is disposed adjacent to tray 1 and supported on the shaft of an AC synchronous motor 33. Reagent tray 31 is adapted to be unidirectionally advanced by motor 33 to selectively position an appropriate reagent below the aspirating/dispensing probe 37. Probe 37 is adapted, under the control of drive mechanism 38, for vertical reciprocal movement and for directional rotational movement, as indicated by the arrows, so as to be selectively positioned over and immersed into reagent container 35 and into a cuvette 3 selectively advanced to reagent-dispense station R. Probe 37 operates to aspirate a precise volume of reagent contained in such container 35 and dispense or load the same into such cuvette 3.

Probes 29 and 37 may be of the aspirating/dispensing type described in U.S. Pat. No. 4,121,466 issued on Oct. 24, 1978, assigned to a common assignee. As described, such probe is normally filled with a pilot fluid which is immiscible with the aqueous liquid, i.e., sample or reagent, to be aspirated and dispensed. Also, an immiscible liquid is flowed downwardly, at a controlled rate, over the outer probe surface, to coat and prevent contact of such surface with the liquid to be aspirated. Accordingly, contamination is positively avoided between the successive liquids, whether sample or reagent, into which the probe is immersed. During the actual aspiration and dispense cycles, the flow of immiscible liquid over the probe surface may be discontinued. The operation of probes 29 and 37 are hereafter more particularly described.

The contents of cuvettes 3 are colorimetrically analyzed, in turn, at read-out station RO, to quantitate the particular analyte for which the contained sample has been reacted. Station RO comprises a light source 39 and collimating lens 41 for directing a beam of light through walls 5 and 7 of cuvette 3 positioned thereat. A detector 43 is located to receive the emerging light beam and generates an electrical signal indicative of the color depth, or analyte concentration, of the reacted sample disposed between windows 5 and 7. Also, a multi-filter wheel 45 is interposed between collimating lens 41 and wall 5 of positioned cuvette 3, which determines the wavelength of the light beam. As is known, a particular analyte is normally absorptive of light of a particular wavelength, the degree of absorption being indicative of the analyte concentration in the reaction sample. The output signal of detector 43 is directed to a register 47, which is adapted to store said signals, on an individual sample basis.

The operation of the system of FIG. 1 is under the control of a controller 49, which is inputted by an operator to identify, as to source patient, each sample loaded in sample tray 23 and, also, indicate the particular analysis to be effected of each such sample. According to such inputs, controller 49 implements a number of sub-routines for controlling the various components of the system to selectively analyze each such sample, as hereafter described.

Figure 2:
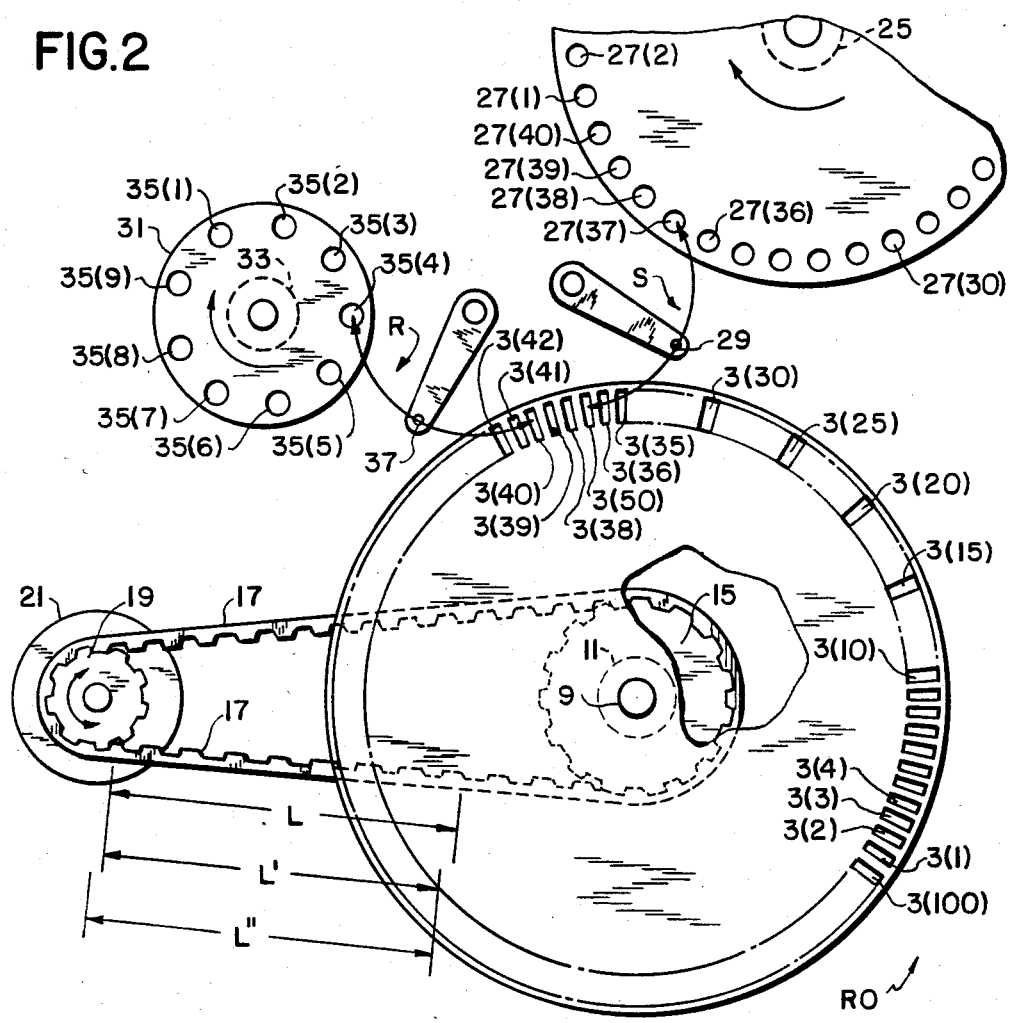
FIG. 2 is a top view of the biochemical analyzer of FIG. 1.
Figure 3:
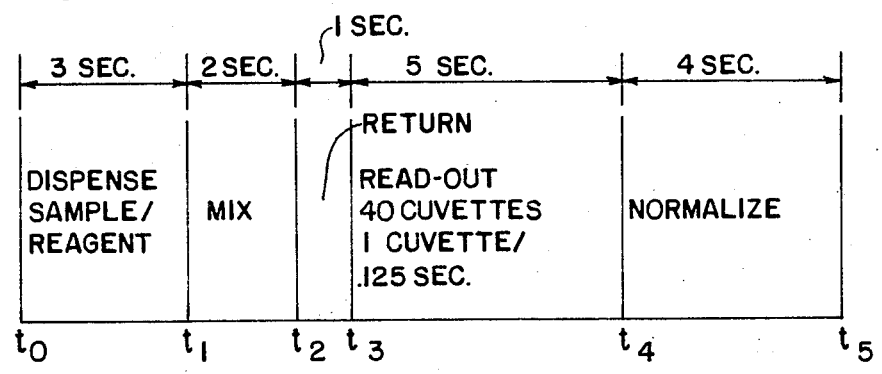
FIG. 3 is a timing diagram illustrating a single operational cycle of the biochemical analyzer of FIG. 1.

The operation of the analytical system of the present invention is more readily understood by reference to FIGS. 1, 2 and 3, wherein like references have been used to denote corresponding structure. For purposes of description, it is assumed that (1) tray 1 comprises one-hundred cuvettes 3, (2) forty indexing positions of tray 1 are defined between station R and station RO, and (3) three indexing positions of tray are defined between station R and station S. It is further assumed that, at least, cuvettes 3(1) through 3(35) of FIG. 2 have had both reagent and sample dispensed therein and, also, cuvettes 3(36) through 3(39) have had reagent dispensed therein preparatory to the dispensing therein of sample contained in receptacles 27(36) through 27(39), respectively, at station S.

Under such system conditions, controller 49 operates under appropriate sub-routines to operate motor 33 to locate at station R an appropriate receptacle 35, e.g., receptacle 35(4), containing the appropriate reagent to react with sample contained in sample receptacle 27(40); to operate motor 25 to advance the next receptacle 27 (37) containing the sample to be reacted in the reagent-loaded cuvette 3(37) at station S and into which an appropriate reagent has been previously dispensed; and to operate stepping motor 21 to advance cuvettes 3(37) over 3(40) to stations S and R, respectively. Thereafter, controller 49 operates drive mechanisms 30 and 38 to concurrently control probes 29 and 37, respectively, to aspirate appropriate volumes of sample and reagent, respectively, from receptacles 27(37) and 35(4) and to dispense the same into cuvettes 3(37) and 3(40) positioned at stations R and S, respectively. Such dispensing operation occurs during time interval $t_0$–$t_1$ of FIG. 3, which may be of three-seconds duration.

Following the dispensing cycle and when drive mechanisms 30 and 38 have normalizing probes 29 and 37, respectively, over sample tray 23 and reagent tray 31, respectively, controller 49 operates stepping motor 21 to advance tray 1 in short, rapid incremental steps, to mix the contents of each "loaded" cuvette 3 during time interval $t_1$–$t_3$, which has a two-seconds duration. For example, tray 1 may be advanced or indexed, say, twenty-eight angular positions, with a momentary abrupt stop at each position. Such mixing is effected in incremental steps shorter and, also, at a rate faster than the normal indexing of tray 1. During the mixing cycle, the contents of all "loaded" cuvettes 3 are sufficiently agitated to insure thorough mixing of their contents. Following the mixing cycle, at time $t_2$, controller 49 reverses stepping motor 21 to normalize tray 1 by returning cuvette 3(36) and 3(40) to stations S and R, respectively, and to reposition cuvette 3(1) at station RO. Normalization of tray 1 is effected during time interval $t_2$–$t_3$, which may have a one-second duration.

Following the mixing and normalizing cycles, at time $t_3$, controller 49 operates stepping motor 21 to normally index tray 1 in a clockwise direction, to advance cuvettes 3(1) through 3(40), in turn, to station RO. Synchronously controller 49 operates wheel 45 to selectively position an appropriate filter to pass light an appropriate wavelength through each of the cuvettes 3(1) through 3(36), in turn, to effect a particular analyte analysis. As only reagent is present in cuvettes 3(37) through 3(40), the output of detector 43 in respect of each such cuvette is stored as the base line for the subsequent quantitation of a particular analyte to be subsequently analyzed in such cuvettes. The successive outputs of detector 43 are stored in register 47, under the control of controller 49, according to the source patient identified by the operator in respect of cuvettes 3(1) through 3(40). For purposes of description, tray 1 may be indexed one position each 0.125 second, such that cuvettes 3(1) through 3(40) are read out during time interval $t_3$–$t_4$ which may have a five-second duration.

When the read-out cycle has been completed at time $t_4$, cuvette 3(40) is located at station RO and the contents of each of cuvettes 3(1) through 3(40) have been successively analyzed and the analytical results appropriately stored in register 47. During time interval $t_4$–$t_5$, which may have a four-second duration, controller 49 operates stepping motor 21 to rotate tray 1 in a counter-clockwise direction, to normalize the system preparatory to a next dispensing cycle. Preferably, the reverse indexing of tray 1 duplicates the forward indexing of tray 1, except for being effected in a reverse direction. Also, the reverse indexing of tray 1 is terminated when cuvette 3(2) is located at station RO, cuvette 3(41) is located at station R, and cuvette 3(37) is located at station S, that is, tray 1 is reverse indexed to one angular position less than it had been forward-indexed. It should be appreciated, however, that tray 1 can be reverse indexed to any number of angular positions, depending upon the particular requirements of the system.

When the system of FIG. 1 is normalized at time $t_5$, controller 49 commences a next operating cycle by operating motor 25 to advance the next receptacle 27(38) to station S and motor 33 to advance, for example, receptacle 35(3) to station R. Thereupon, controller 49 operates drive mechanisms 30 and 38 to control probes 29 and 37, respectively, to aspirate and dispense appropriate volumes of sample from receptacle 27(38) and reagent from receptacle 35(3) into cuvettes 3(38) and 3(41), respectively, located at stations S and R, respectively. As mentioned above, reagent dispensed into cuvette 3(41) is intended for reaction with the sample contained in receptacle 27(41), which will be dispensed into cuvette 3(41) when advanced to station S.

Upon completion of the aspirate/dispense cycle, at time $t_1$, controller 49 operates stepping motor 21 to effect a next mixing cycle, as described above, to agitate and mix the contents of all "loaded" cuvettes 3 in tray 1 and to subsequently return tray 1, at time interval $t_3$, to reposition cuvettes 3(41), 3(37), and 3(2) at stations R, S and RO, respectively. Thereafter, stepping motor 21 is operated by controller 49 to advance each cuvette 3(2) through 3(41), in turn, through station RO, whereat the contents of such cuvettes are analyzed, in turn, and the analytical results, i.e., the output of detector 43, are stored in register 47 in respect of the corresponding source patients, as described above. When cuvette 3(41)

is located at station RO, controller 49 operates motor 21 to rotate tray 1 in a counterclockwise direction. Tray 1 is reverse indexed through thirty-nine angular positions, to locate cuvette 3(3) at station RO, cuvette 3(42) at station R and cuvette 3(39) at station S, preparatory to a next operational cycle.

It is evident that during normal operation, forty distinct analyses will be made of the contents of each cuvette 3, the analytical results being stored in correlated fashion in register 47 in respect of source patient, whose identification was initially inputted to controller 49. As multiple readouts are made of each cuvette, register 47 is operated to use only selected ones of such readings in the calculation and printing out the final analytical results identified with the appropriate source patients. Generally, in respect of zero-order rate reactions, nine selected readouts may be used to calculate the analyte concentration by a conventional "best fit" technique. Also, in respect of first-order rate reactions, two readouts only need be used in the calculation of the analyte concentration, one being the initial "base line" readout of the corresponding cuvette 3 prior to sample addition. Finally, in respect of end-point reactions, both the "base line" readout and one additional readout are used to calculate the analyte concentration. The calculation techniques employed are well-known in the art.

As successive readouts are required to calculate analyte concentration and to insure accurate analytically results, the successive positionings of each cuvette at station RO, at least, must be exactly duplicated. Such exact repositioning insures that variations in the light transmission properties due to transmission or geometric non-uniformities of the walls 5 and 7 of each cuvette 3 are cancelled out for each successive measurement, that is, such variations are constant for each measurement. Exact repositioning is achieved by rotating tray 1 a reverse direction, so as to normalize the system, whereby the relationship of belt 17 and drive pulleys 15 and 19 is fixed and invariable in respect to the positioning of each individual cuvette 3 at a treatment station, say, RO. A same length of belt 17 is used in successively positioning each cuvette 3 at station RO. For example, and considering cuvette 3(40) positioned at station R, such cuvette is indexed during the read-out cycle, at time $t_3-t_4$, through forty angular positions by passage of a section L of belt 17 over drive pulley 19, as indicated in FIG. 3. During such read-out cycle the passage of section L', of belt 17 over drive pulley 19 equivalent to thirty-nine angular positions, is effective to position cuvette 3(39) at station RO. During the normalizing cycle, at time $t_4-t_5$, section L' of belt 17 is returned over drive pulley 19 to locate cuvette 3(41) at station R, cuvette 3(40) having been normalized to one angular position beyond station R. During the next read-out cycle, a section L' of belt 17, including section L' and equivalent to forty angular positions of tray 1, is passed over drive pulley 19 to advance cuvette 3(41) to station RO. The passage of section L' of belt 17 over drive pulley 19, at this time, is effective to advance cuvette 3(40) through thirty-nine angular positions to be exactly repositioned at station RO. Any dimensional errors in those portions of belt 17 actually engaging pulleys 15 and 19 or either of the pulleys will affect the positioning of cuvette 3(39) at station RO. It is evident that, however, as there is no play or slippage between belt 17 and pulleys 15 and 19 and because of the reversal of belt 17 during each normalizing cycle, the relationship of such belt to each of the pulleys will be exactly duplicated during each repositioning of each cuvette 3(39) at station RO. Therefore, any dimensional error in those portions of belt 17 engaging pulleys 15 and 19 or in either of such pulleys is effectively cancelled, i.e., exactly duplicated, during each such repositioning. Accordingly, if any tooth-to-tooth dimensional error should exist in any portion of belt 17 or in any portion of either of the pulleys 15 and 19, a positioning error is introduced only when such portion of belt 17 engages either of pulleys 15 or 19 or when such portion of the pulley is engaged by belt 17 and would affect only the initial alignment or positioning of a particular cuvette at a treatment station, say, RO. However, since the relationship of belt 17 and pulleys 15 and 19 is fixed with respect to each cuvette, a same positioning error is re-introduced during each successive repositioning of such cuvette at a treatment station, whereby the position of such cuvette is exactly duplicated. In prior art discrete-type analyzers, a repositioning of a cuvette at a particular station requires a complete revolution of tray 1 and, unless the drive belt, such as 17, is exactly equal to that length required to rotate tray 1 through one revolution, the relationship of the drive belt to the driving pulleys is not fixed and invariable with respect to each cuvette and any tooth-to-tooth dimensional errors would be cumulative, whereby an exact repositioning of each such cuvette at a particular treatment station could not be duplicated.

What is claimed is:

1. A method for effecting multiple colorimetric measurements of a liquid sample contained in a selected cuvette carried on a bidirectionally rotatable cuvette tray supporting a plurality of cuvettes, each cuvette being provided with opposing transparent walls to define a sight passageway for the reading of liquid sample contained therein at a read-out station, which method comprises:
   (1) locating a selected cuvette in a liquid dispensing station and dispensing liquid therein;
   (2) rotating said cuvette tray in a first direction and stopping the rotation of the tray to locate said selected cuvette at a read-out station;
   (3) colorimetrically measuring said liquid in said selected cuvette at said read-out station to generate a first signal;
   (4) rotating said cuvette tray in a second and opposite direction;
   (5) repositioning said selected cuvette at said read-out station by rotating said cuvette tray in said first direction and stopping the rotation to locate said cuvette at said read-out station, wherein by using the same section of the drive system said cuvette is thereby accurately repositioned at said read-out station in order that the same portion of said opposing transparent walls define said sight passageway;
   (6) colorimetrically measuring the liquid in said selected cuvette following the repositioning of said selected cuvette at said read-out station to generate a second signal; and
   (7) storing said first and second signals.

2. The method of claim 1 wherein rotating said cuvette tray in said second and opposite direction comprises positioning one of said plurality of cuvettes at a liquid dispensing station.

3. The method of claim 2 wherein rotating said cuvette tray in said first direction of step 2 comprises rotating said cuvette tray through N angular positions in said first direction and rotating said cuvette tray in said second and opposite direction comprises rotating said cuvette tray less than N angular positions.

4. The method of claim 1 which further comprises mixing the contents of said selected cuvette prior to colorimetrically measuring said liquid.

5. The method of claim 4 wherein said mixing comprises advancing said cuvette tray in said first direction in incremental steps with a momentary abrupt stop after each step.

6. A method for effecting multiple colorimetric measurements of liquid samples contained in a plurality of cuvettes supported on a bidirectionally rotatable cuvette tray, each cuvette being provided with opposing transparent walls to define a sight passageway for measuring the liquid sample contained therein, wherein at least one treatment station and at least one read-out station are positioned with respect to said cuvette tray, which method comprises:
  (1) introducing reagent into successive cuvettes positioned, in turn, at a first treatment station;
  (2) introducing sample to be reacted into said reagent-containing successive cuvettes positioned, in turn, at a second treatment station and reacting said sample;
  (3) rotating said cuvette tray subsequent to the positioning of selected cuvettes at said treatment stations to mix the contents thereof by advancing said cuvette tray in incremental steps with a momentary abrupt stop after each step;
  (4) rotating said cuvette tray in a first direction subsequent to the mixing of the contents of said selected cuvettes to pass a number of said mixed cuvettes through a read-out station; and
  (5) subsequently rotating said cuvette tray in a second and opposite direction and stopping the rotation of said tray to position each of said mixed cuvettes which has been passed through said read-out station, in turn, at said read-out station by using the same section of the drive system such that the same portions of said opposing transparent walls define said sight passageway, in order to colorimetrically measure the contents thereof.

7. The method of claim 6 comprising the further step of positioning a next successive cuvette at said treatment station during rotation of said cuvette tray in said second direction, as in step (5).

8. The method of claim 6 wherein step (4) comprises rotating said cuvette tray a number N of angular positions in said first direction and step (5) comprises rotating said cuvette tray a number of angular positions less than N in said second direction.

9. The method of claim 8 wherein at least a portion of step (5) is effected at a same or faster rate than step (4).

10. The method of claim 9 comprising the further step of normalizing said cuvette tray by rotating in said second direction, as in step (5), to position a next successive cuvette at said treatment station.

11. The method of claim 8 wherein step (5) comprises rotating said cuvette tray a number of angular positions equal to N−1 in said second direction.

12. A method for effecting multiple colorimetric measurements of liquid samples contained in a plurality of cuvettes supported on a bidirectionally rotatable cuvette tray, each cuvette being provided with opposing transparent walls to define a sight passageway for measuring the liquid sample contained therein, wherein at least one treatment station and at least one read-out station are positioned with respect to said cuvette tray, which method comprises:
  (1) introducing sample to be reacted into successive cuvettes positioned, in turn, at a first treatment station.
  (2) introducing reagent into said sample-containing successive cuvettes positioned, in turn, at a second treatment station, and reacting said sample;
  (3) rotating said cuvette tray subsequent to the positioning of selected cuvettes at said treatment stations to mix the contents thereof by advancing said cuvette tray in incremental step with a momentary abrupt stop after each step;
  (4) rotating said cuvette tray subsequent to the mixing of the contents of said selected cuvettes to pass a number of said mixed cuvettes through a read-out station; and
  (5) subsequently rotating said cuvette tray in a second and opposite direction and stopping the rotation of said tray to position each of said mixed cuvettes which has been passed through said read-out station, in turn, at said read-out station by using the same section of the drive system such that the same portions of said opposing transparent walls define said sight passageway, in order to colorimetrically measure the contents thereof.

13. The method of claim 12 comprising the further step of positioning a next successive cuvette at said treatment station during rotation of said cuvette tray in said second direction, as in step (5).

14. The method of claim 12 wherein step (4) comprises rotating said cuvette tray a number N of angular positions in said first direction and step (5) comprises rotating said cuvette tray a number of angular positions less than N in said second direction.

15. The method of claim 14 wherein at least a portion of step (5) is effected at a same or faster rate than step (4).

16. The method of claim 15 comprising the further step of normalizing said cuvette tray by rotating in said second direction, as in step (5), to position a next successive cuvette at said treatment station.

17. The method of claim 14 wherein step (5) comprises rotating said cuvette tray a number of angular positions equal to N−1 in said second direction.

* * * * *